(12) United States Patent
Gorkovenko

(10) Patent No.: US 10,596,262 B2
(45) Date of Patent: *Mar. 24, 2020

(54) POLYMER COMPOSITIONS IN BIOMEDICAL APPLICATIONS

(71) Applicant: Alexander A Gorkovenko, Mission Viejo, CA (US)

(72) Inventor: Alexander A Gorkovenko, Mission Viejo, CA (US)

(73) Assignee: TRGel, LLC, Mission Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,283

(22) Filed: Jun. 19, 2015

(65) Prior Publication Data

US 2016/0367679 A1     Dec. 22, 2016

Related U.S. Application Data

(63) Continuation-in-part of application No. 13/205,247, filed on Aug. 8, 2011, now Pat. No. 9,149,791.

(51) Int. Cl.
| | |
|---|---|
| *A61K 47/34* | (2017.01) |
| *A61K 38/47* | (2006.01) |
| *A61K 9/14* | (2006.01) |

(52) U.S. Cl.
CPC .............. *A61K 47/34* (2013.01); *A61K 9/146* (2013.01); *A61K 38/47* (2013.01); *C12Y 302/01017* (2013.01)

(58) Field of Classification Search
CPC ........ A61K 47/64; A61K 38/47; A61K 9/146; C12Y 302/01017
See application file for complete search history.

(56) References Cited

U.S. PATENT DOCUMENTS

| | | | |
|---|---|---|---|
| 5,877,224 A | 3/1999 | Brocchini et al. | |
| 6,287,588 B1* | 9/2001 | Shih ........................ | A61K 47/34 424/426 |
| 7,354,747 B1 | 4/2008 | Guan | |
| 8,632,809 B2 | 1/2014 | Asgahrian et al. | |
| 8,642,502 B2* | 2/2014 | Gorkovenko ............ | A61K 8/86 502/402 |
| 8,673,264 B2 | 3/2014 | Baylatry et al. | |
| 8,691,791 B2 | 4/2014 | Lewis et al. | |
| 2005/0008609 A1* | 1/2005 | Cohn ...................... | A61K 47/34 424/78.1 |
| 2009/0202642 A1* | 8/2009 | Huang .................. | A61K 9/0024 424/488 |
| 2012/0046435 A1* | 2/2012 | Gorkovenko .......... | B01J 20/286 527/300 |

* cited by examiner

*Primary Examiner* — Sean M Basquill
(74) *Attorney, Agent, or Firm* — Gary L. Loomis; G. L. Loomis & Associates, Inc.

(57) ABSTRACT

The present invention relates to biomedically useful compositions of C2-C3 linked polyethers of 1,6:2,3-dianhydrohexopyranose derivatives combined with effective amounts of one or more bioactive agents. In certain embodiments the C2-C3 linked polyether of a 1,6:2,3-dianhydrohexopyranose derivatives are aqueous insoluble. In certain other embodiments biomedically useful compositions have the physical form of microparticles, microspheres, tubes, rods, sheets, membranes, fibers and the like. In certain embodiments the bioactive agent is a protein.

17 Claims, No Drawings

POLYMER COMPOSITIONS IN BIOMEDICAL APPLICATIONS

CROSS-REFERENCE TO RELATED APPLICATION

This application is a continuation-in-part of U.S. application Ser. No. 13/270,144 filed Apr. 12, 2012. This application also claims the benefit of priority under 35 U.S.C. § 119(e) of U.S. Provisional Application No. 61/926,922 filed Jan. 13, 2014, and U.S. patent application Ser. No. 13/205,247 all of which are herein incorporated by reference.

FIELD OF THE INVENTION

The present invention relates to novel carbohydrate polyether compositions useful in biomedical applications. More specifically the invention relates to novel carbohydrate polyether compositions particularly suited for treating a vascular defect in a mammalian body by embolization of a targeted blood vessel site. Such compositions also relate to the controlled release of bioactive substances within a mammalian body.

BACKGROUND

Therapeutic embolization is the intentional endovascular occlusion of a mammalian artery or vein. Historically, the first agent used for embolotherapy was autologous blood clot. This was easily and quickly obtained and was inherently biocompatible. The drawback of autologous blood clot is that as the body's natural clot lysis dramatically limits the durability of occlusion; recanalization can recur within hours to days. The next agents developed were fascial strips harvested from dura and tensor fascia lata. Silk threads were also historically used as embolic agents, notably for intracranial vascular malformations, however, with the advent of modern liquid and particulates, silk, clot, and fascia are no longer commonly used.

Numerous embolic materials and devices have been described during the last 40 years. Modern embolic agents are either temporary or permanent. Permanent agents are more common, and there are many applicable subsets including liquid agents, particulates, coils, detachable plugs and balloons.

Use of mechanical embolic devices such as detachable embolic coils and balloons are well known in the art. Embolic coils are typically used for occlusion of larger vessels and cause complete occlusion equivalent to surgical ligation. Coils cause vessel occlusion by inducing thrombosis. Deployment of a coil acts by physically slowing or stopping blood flow, providing a thrombogenic surface for clot formation, and causing vessel wall damage that results in release of thrombogenic factors. Bare coils can only partially embolize vessels by pure mechanical occlusion. Because coil embolization depends on the ability of the patient to form thrombus, coagulopathic states such as thrombocytopenia, platelet dysfunction, and abnormal clotting factors may hinder complete vessel occlusion. Time to occlusion also depends on the type of coil used, as well as the rate of flow of the target vessel embolized. Certain detachable embolic coils are electrolytically detachable (see Guglielmi et al. *J Neurosurg* 1991; 75:11-17), while others, known as hydrogel coils are detachable platinum coils coated with an expandable polymer (see Kallmes et al. Am J Neuroradiol 2002; 23(9):1580-1588). Another published article (AJNR: 6, July/August 1985) describes the use of detachable coils and balloons in conjunction with embolization procedures in polyvinyl alcohol (PVA) sponge, gelatin sponge, or isobutyl-2 cyanoacrylate (IBCA).

Various forms of gelatin foam have been used as an intravascular embolization agent for more than 30 years, with the first intravascular use in 1964 for cavernous carotid fistulas (J Neurosurg 1964; 21: 303-315). Since that time, gelatin foam has evolved into a common agent used for a variety of applications. Gelatin foam is a biologic substance made from purified skin gelatin. It is commonly available as Gelfoam® from Pharmacia and Upjohn Co (division of Pfizer Inc. New, York, N.Y.) in sterile sheets and as a powder comprised of 40 to 60 mm particles. Sheets can be cut into a variety of shapes. Gelfoam® cut into small 1 to 2 mm pieces can be mixed with dilute contrast and injected as pledgets, or be prepared as slurry. Another embolic use of gelatin foam is to form a small torpedo that can be injected into the target vessel for a more proximal occlusion. Gelatin foam causes mechanical obstruction, slowing blood flow and hastening thrombus formation and additionally provides a scaffold for clot formation. Gelfoam® embolization provides temporary vessel occlusion, allowing recanalization in a few weeks. The temporary nature of gelatin foam occlusion can be either an advantage or disadvantage depending on the clinical situation (e.g., temporary nature is advantageous in case of hemoptysis or trauma). However, has disadvantages since it has been postulated that Gelfoam® can be associated with infection due to trapped air bubbles. Furthermore, gelatin foam powder can potentially cause ischemia due to the small size (especially at sizes<70 mm) of the particles, allowing distal embolization.

Another common embolic material is polyvinyl alcohol (PVA). Polyvinyl alcohol was first introduced as an intravascular embolization agent in 1974 in the form of a sponge, current intravascular use of polyvinyl alcohol (PVA) (available from Boston Scientific/Target Therapeutics, Cork Ltd., Cork, Ireland and Cordis J&J Endovascular, Miami, Fla.) is primarily in the form of particles. The particles are made from a PVA foam sheet that is vacuum dried and rasped into particles. The particles are filtered with sieves and are available in sizes ranging from 100 mm to 1100 mm. Polyvinyl alcohol particles provide permanent occlusion by adherence to the vessel wall, causing stagnation of flow; in addition to lodging in the smallest vessel into which they will fit. The results are an inflammatory reaction and focal angionecrosis, with vessel fibrosis developing over time. Polyvinyl alcohol particles are biocompatible, and there is vast cumulative clinical experience with PVA particle embolization. The major disadvantage of PVA particles is their tendency to aggregate, occluding vessels more proximally than might be expected based on stated size. Particle clumping can also cause catheter occlusion, which is preventable by dilution of particles, proper suspension, and slow infusion. In addition, PVA particles can accumulate in the catheter hub and theoretically cause subsequent non-target embolization when the catheter is flushed.

Another common embolic material is tris-acryl gelatin microspheres (TAGM) are useful for uterine fibroid embolization. Such materials are fabricated from an acrylic polymer matrix impregnated and embedded with porcine gelatin. They are non-resorbable hydrophilic particles that are precisely calibrated by size. In addition, tris-acryl gelatin microspheres can be temporarily compressed by 20 to 30% of their initial diameter. While embolic polyvinyl alcohol particles are known to be irregular nature, tris-acryl gelatin microspheres are smooth and spherical in shape and fragmentation is 100 not observed. Disadvantages of tris-acryl gelatin microspheres include the need for intermittent agitation to prevent sedimentation and maintain suspension. In addition, tris-acryl gelatin microspheres are partly composed of porcine gelatin, which has allergic potential.

Yet another common embolic material is ethylene vinyl alcohol copolymer (EVOH) (commercially available as Onyx®, from Micro Therapeutics, Inc., Irvine, Calif.). The material is a copolymer of ethylene and vinyl alcohol prepared with dimethyl sulfoxide (DMSO) as solvent. Tantalum powder is usually added for opacity. Upon prolonged contact with blood, the DMSO diffuses away allowing dissolution of the EVOH, which forms a solid in the blood vessel. It was has been used as an embolic since 1990 and has been used as an embolic agent for cerebral arterio-venous malformation since 2005. It has also been used for treatment of cerebral aneurysms.

Also known as an embolic agent is calcium alginate gel (available as ALGEL® from Neural Intervention Technologies, Ann Arbor, Mich.), which has been evaluated primarily for neuro-endovascular procedures. It is comprised of a polymer of alginic acid, which is a natural polysaccharide gel obtained as its water-soluble sodium salt (sodium alginate) from brown algae. When exposed to a divalent salt such as calcium chloride, the sodium alginate forms an insoluble a non-adhesive alginate gel matrix. Calcium alginate gel occlusion of AVMs and aneurysms in a swine model has been reported (Becker et al. Neurosurgery 2007; 60: 1119-1128 and Becker et al. Neurosurgery 2005; 56: 793-801).

Cyanoacrylate adhesives such as n-butyl-2 cyanoacrylate (NBCA) are well known in the art. Cyanoacrylate-based embolics have been used for various medical procedures in humans such as cerebral AVM embolization, treatment of extra-cerebral, spinal tumors, spinal AVMs and arterio-venous fistulas (AVFs), embolization of brain and spinal cord tumors, cerebral AVMs, and brain and spinal cord dural AVFs. Medical grades of n-butyl-2 cyanoacrylate are available (TruFill® from Cordis, Miami Lakes, F.L. and as Glubran® from Gem, Viareggio, Lucca, Italy). Also know are cyanoacrylate embolic agents comprising 2-hexyl-cyanoacrylate combined with an esterified fatty acid to retard polymerization and gold particles to provide radiopacity (U.S. Pat. No. 6,037,366; RE39,150; 6,476,070; 6,538,026; RE42,377 and 6,476,069). Such cyanoacrylate adhesives are generally supplied as a monomer, which is clear and free flowing liquid, which polymerizes upon contact with an aqueous environment such as blood or water. The rate of polymerization is largely dependent on the pH of the aqueous system to which it is exposed. Tantalum powder is often incorporated to provide radiographic opacification, but is also known to retard the initiation of polymerization. Disadvantages of cyanoacrylate-based embolics include acute inflammatory reaction in the vessel wall, which progresses to chronic inflammation and fibrosis or recanalization if only partial embolization is achieved.

In traditional drug delivery systems, such as oral ingestion or intravascular injection, the bioactive agent is distributed throughout the body through the systemic blood circulation and therefore, for most therapeutic agents only a small portion of the medication reaches the desired site. Targeted drug delivery seeks to concentrate the medication in the tissues of interest while reducing the relative concentration of the medication in the remaining tissues. Bioactive agent filled polymers (both biodegradable and non-biodegradable) are used in the form of particles, microspheres, stents, implantable devices, films, foams, coatings and the like to provide a time related gradual release profile of the bioactive agent.

Therefore a need exists for improved embolic compositions and devices which have no adverse effects on surrounding normal tissue and which do not exhibit carcinogenic or teratogenic potential. A further need exists for embolic compositions that can be rapidly administered. Another need exists for embolic compositions that are also useful for the incorporation and subsequent controlled release of bioactive substances within a mammalian body and a still further need exists for controlled release of bioactive substances from solid implants formed in situ at a desired site in a mammalian body.

SUMMARY OF THE INVENTION

The embodiments of the present invention relate generally to novel synthetic biocompatible carbohydrate polymer compositions, which useful as components of embolic systems useful for treating a vascular defect, such as aneurysms, arterio-venous malformations (AVM's), fistulas or other diseased or deformed vessels in the mammalian vasculatures as well as other similar biomedical applications. Such systems comprise a solution of an aqueous insoluble C2-C3 linked polyether of a 1,6:2,3-dianhydrohexopyranose derivative in a biocompatible solvent, wherein the biocompatible solvent is miscible or soluble in aqueous media, such as body fluids. In such embodiments the solution is introduced to a desired site of a blood vessel, wherein upon contact with body fluids the biocompatible solvent diffuses away whereupon the biocompatible C2-C3 linked polyether of a 1,6:2,3-dianhydrohexopyranose derivative precipitates to form an occlusion.

Also, certain polymer compositions of the present invention are useful as excipients for controlled release of bioactive agents into targeted areas within mammalian bodies. Such targeted drug delivery systems seek to concentrate the bioactive agent or pharmaceutical in the tissues of the targeted areas while reducing the relative concentration of the medication in the non-targeted tissues. Bioactive agent filled polymer compositions (both biodegradable and non-biodegradable) are used in the form of particles, microspheres, stents, implantable devices, films, foams, coatings and the like to provide a time related gradual release profile of the bioactive agent.

More specifically such embodiments relate to compositions of non-carbohydrate polymers of poly(2-3)-1,6-anhydroglucopyranoses, and derivatives thereof, with controlled weight-average molecular weights, narrow polydispersity indices, controlled microstructures, controlled tertiary structures, controlled glass transition temperatures, and controlled hydrophilicity or hydrophobicity, wherein the polymer compositions are biocompatible and in certain embodiments biodegradable.

Suitable poly(2-3)-1,6-anhydroglucopyranoses are prepared by an anionic ring-opening living polymerization of 1,6:2,3-dianhydrohexopyranoses (Cerny epoxides) by known methods. Since the resulting 2-3 linked carbohydrate polyethers do not have glycosidic bonds between monomer units, such carbohydrate polyethers are not polysaccharides. Furthermore these synthetic polyether carbohydrates can exhibit a polydispersity index (PDI) considerably less than 2.0, which is considerably lower than the PDI for nearly all carbohydrate polymers found in nature as well as most man-made polymers. Also, the chain length of such polymers is readily controlled and may be manipulated to serve the needs of specific applications. Additionally, the synthetic carbohydrate polyethers of the present invention produced via anionic living polymerization techniques are useful in the production of a variety of derivatives with carefully controlled molecular structures.

The present invention also provides compositions and formulations comprising water-soluble and water-insoluble synthetic carbohydrate polyethers with a large degree of structural variation achieved by choice of substituents in the 1,6:2,3-dianhydrohexopyranoses monomers as well as by post-polymerization functionalization.

Furthermore, the carbohydrate polyethers useful in embodiments of the present invention, can be linear or non-linear and can be homopolymers, copolymers or combinations thereof. The non-linear polymers of the invention can have a variety of architectures, including for example star-polymers, branched polymers, graft polymers, cross-linked polymers, semi-cross-linked polymers and the like or combinations thereof. These various polymer architectures are achieved with a high degree of control by the polymer preparation methods of the invention. Since the synthetic, non-polysaccharide, carbohydrate polyethers useful in compositions and formulations of the present invention are essentially monodisperse and uniform in structure, the biomedically useful formulations produced therefrom are consistent with little or no batch-to-batch variability.

Certain embodiments of the present invention relate to biomedically useful compositions comprising an aqueous insoluble C2-C3 linked polyether of a 1,6:2,3-dianhydrohexopyranose derivative intimately associated or in intimate association with one or more bioactive agents. In certain of such embodiments the compositions can have physical forms including, but not limited to, microparticles, microspheres, tubes, rods, sheets, membranes and fibers, which are formed by known techniques, such as grinding, extrusion, molding, casting, spray drying and the like.

In certain of these embodiments wherein the aqueous insoluble C2-C3 linked polyether of a 1,6:2,3-dianhydrohexopyranose derivative has a physical form selected from the group consisting of microparticles, microspheres, tubes, rods, sheets, membranes and fibers and the like. The microparticles or microspheres of these embodiments have an average diameter between 5 and 2000 microns. In certain of these embodiments the physical form of the C2-C3 linked polyether of a 1,6:2,3-dianhydrohexopyranose derivative is porous. In certain of these porous embodiments the total pore volume is in the range between 0.05 cc/g to 5.0 cc/g. In certain embodiments wherein the physical form is porous, the average pore diameter is in the range of 0.001 mm to 0.05 mm.

In certain embodiments the bioactive agent is uniformly dispersed throughout the C2-C3 linked polyether of a 1,6:2,3-dianhydrohexopyranose derivative. In certain other other embodiments the bioactive agent is in the form of a coating on the surface of the C2-C3 linked polyether of a 1,6:2,3-dianhydrohexopyranose derivative in one or more of the various physical forms described above.

In certain embodiments the C2-C3 linked polyether of a 1,6:2,3-dianhydrohexopyranose derivative is bioresorbable.

In certain other embodiments the bioactive agent is aqueous soluble. In certain embodiments the protein includes, but is not limited to enzymes, monoclonal antibodies, fusion proteins, vascular endothelial growth factor (VEGF) or VEGF inhibitor and the like. In certain other embodiments the bioactive agent is a small molecule drug.

Certain embodiments are related to biomedically useful compositions comprising a solution of the aqueous insoluble C2-C3 linked polyether of a 1,6:2,3-dianhydrohexopyranose derivative and a bioactive agent in a biocompatible solvent.

In certain embodiments the C2-C3 linked polyether of a 1,6:2,3-dianhydrohexopyranose derivative further comprises one or more linkages chosen from the group consisting of an ester linkage, a urethane linkage, a carbonate linkage and an anhydride linkage.

In certain of these embodiments the C2-C3 linked polyether of a 1,6:2,3-dianhydrohexopyranose derivative is bioresorbable. In certain embodiments polyether of a 1,6:2,3-dianhydrohexopyranose derivative has a weight average molecular weight in the range of about 2 to 350 kDa, while in certain preferred compositions the polyether of a 1,6:2,3-dianhydrohexopyranose derivative has a weight average molecular weight in the range of about 3 to 150 kDa. In certain embodiments the polyether of a 1,6:2,3-dianhydrohexopyranose derivative has a polydispersity index less than or equal to 1.5. In certain embodiments the polyether of a 1,6:2,3-dianhydrohexopyranose derivative has a polydispersity index within the range of about 1.05 to 1.15.

In certain of the embodiments relating to a solution of an aqueous insoluble C2-C3 linked polyether of a 1,6:2,3-dianhydrohexopyranose derivative in a biocompatible solvent the total composition comprises from about 2.5 to about 25 weight percent of the polyether of a 1,6:2,3-dianhydrohexopyranose derivative. In certain preferred embodiments the total composition comprises from about 2.5 to about 15 weight percent of the polyether of a 1,6:2,3-dianhydrohexopyranose derivative.

In certain of the embodiments relating to a solution of an aqueous insoluble C2-C3 linked polyether of a 1,6:2,3-dianhydrohexopyranose derivative in a biocompatible solvent the biocompatible solvent is an aqueous miscible solvent. In cert of such embodiments the aqueous miscible biocompatible solvent is dimethyl sulfoxide, analogues/homologues of dimethylsulfoxide, ethanol, acetone, and the like. I certain of such embodiments the aqueous miscible biocompatible solvent is dimethyl sulfoxide. Certain of such embodiments further comprising an aqueous media insoluble contrast agent such as tantalum, tantalum oxide, barium sulfate and the like.

In certain of the embodiments relating to a solution of an aqueous insoluble C2-C3 linked polyether of a 1,6:2,3-dianhydrohexopyranose derivative in a biocompatible solvent the composition further comprises a bioactive agent such as a a small molecule pharmaceutical agent. In certain of such compositions the bioactive agent is chemically bonded to the polyether of a 1,6:2,3-dianhydrohexopyranose derivative.

In certain of the embodiments relating to a solution of an aqueous insoluble C2-C3 linked polyether of a 1,6:2,3-dianhydrohexopyranose derivative in a biocompatible solvent the composition useful for the embolization of a blood vessel.

A method for embolizing a blood vessel includes the set of introducing a sufficient amount of a solution of an aqueous insoluble C2-C3 linked polyether of a 1,6:2,3-dianhydrohexopyranose derivative in a biocompatible solvent to a desired site of the blood vessel, wherein upon contact with body fluids the polyether of a 1,6:2,3-dianhydrohexopyranose derivative precipitates to form a solid mass which at least partially occludes the vessel. Preferably in such methods for embolizing a blood vessel the solution is introduced via an intravascular catheter technique.

DETAILED DESCRIPTION OF THE INVENTION

As used herein, the following terms shall have the following meaning:

"Biodegradable" is synonymous with "bioresorbable" and refers to a material that erodes or otherwise degrades in vivo to afford non-toxic degradation products that may be metabolized or excreted from the body.

"Parenteral administration" refers to any route of pharmaceutical administration other than the alimentary canal, including, for example, subcutaneous and intramuscular.

"Bioactive agent" refers to a biologically active material including, but not limited to, medicinal agents, drug, pharmaceutically active compositions, viable cells including, but not limited to, stem cells, islets cells, fibroblast cells, T-cells, 8-cells, dendritic cells, and the like.

"Effective amount" encompasses, without limitation, an amount of a bioactive composition that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition. Effective amounts of the pharmaceutical formulation will vary according to factors such as the degree of susceptibility, age, gender, and weight of the individual, as well as idiosyncratic responses of the individual. See, e.g., U.S. Pat. No. 5,888,530 issued to Netti, et al, which is incorporated herein by reference.

"Therapeutically effective amount" refers to an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent.

"Diagnostically effective amount" refers to an amount that is sufficient to produce a signal, image, or other diagnostic parameter.

"Intimately associated" and "intimate association" refer to a state produced by a process comprising the steps of introducing the bioactive agent or agents into a solution of the C2-C3 linked polyether of a 1,6:2,3-dianhydrohexopyranose derivative to form a uniform mixture followed by the subsequent drying of the mixture. By such a process the bioactive agent and the C2-C3 linked polyether of a 1,6:2,3-dianhydrohexopyranose derivative in the dried mixture are said to be intimately associated or in intimate association. Such a dried mixture of intimate associated components thus produced can then be formed by known techniques, such as grinding, extrusion, molding, casting, spray drying and the like, into physical forms including, but not limited to, microparticles, microspheres, tubes, rods, sheets, membranes and fibers.

"Extracellular fluid" refers to a biological fluid including, but not limited to, serum, plasma, blood, interstitial fluid, cerebrospinal fluid, secretions, milk, chyme, lymph, bile, sweat, and urine. Such fluids may also comprise a fluid-like colloid or a fluid-like suspension, e.g., whole blood, non coagulated plasma, or plasma with an effective anti coagulant.

"Labeled composition" refers to a composition comprising radioactive isotopes of phosphorous, iodine, sulfur, carbon, stable isotopes, epitope tags, fluorescent dyes, electron-dense reagents, substrates, enzymes, fluorettes and the like, which are detectable, by spectroscopic, photochemical, biochemical, immunochemical, isotopic, enzyme-linked immunoassays or chemical methods. See, e.g., Aozinov and Nolan (1998) Chem. Biol. 5:713-728, which is incorporated herein by reference.

"Reverse thermal gelation (RTG)" is defined as the temperature below which a polymer is soluble and above which the polymer forms a semi-solid, i.e. gels, emulsions, dispersions and suspensions.

"Lower critical solution temperature (LOST)" is defined as the critical temperature below which the components of a mixture are miscible for all compositions. "Lower critical solution temperature (LOST)" is sometimes referred to as lower consolute temperature. Methods for measuring LCST are readily available (See, Tan et al (2009) Biomaterials. 30:6844-6853).

"Polydispersity index" (PDI) also known as heterogeneity index, or simply dispersity, is a measure of the distribution of molecular mass in a given polymer sample. The PDI calculated is the weight average molecular weight ($M_w$) divided by the number average molecular weight ($M_n$). The PDI has a value equal to or greater than 1, and as the polymer chains approach uniform chain length, the PDI approaches unity.

For the purposes of the present invention a living polymerization is, as defined in the IUPAC Compendium of Chemical Terminology, 2nd Edition, 1997, a chain polymerization from which chain transfer and chain termination steps are absent. In many cases, the rate of chain initiation is fast compared with the rate of chain propagation, so that the number of kinetic-chain carriers is essentially constant throughout the polymerization. In effect, a living polymerization continues until the monomer supply has been exhausted and if additional monomer is added to the reaction mixture the polymerization will resume. Therefore, by variation the monomer feed, block copolymers with well-defined block lengths and very defined random copolymers and terpolymers may be conveniently produced. Polymers of uniform molecular weight, i.e. low polydispersity, are characteristic of polymers produced by living polymerization techniques. Also, since the monomer supply is controllable, the chain length may be manipulated to serve the needs of a specific application. Additionally, anionic living polymerization techniques are useful in the production of a variety of polymers with carefully controlled structures including branched polymers, ladder polymers, framework polymers, star polymers, AB type diblock copolymers and ABA type triblock polymers as well as variations and combinations thereof. The carbohydrate polymer structures made according to anionic living polymerization techniques herein described can be produced with a high degree of regiospecificity, stereospecificity and precisely controlled molecular weight, rendering such polymers ideally useful for the applications cited herein.

A 1,6:2,3-dianhydrohexopyranose monomer useful for the synthesis of polymers of the present invention is shown in general structural formula (I) wherein R represents any moiety that does not interfere with anionic living polymerization, i.e., R is a moiety that is weakly reactive or unreactive toward anions and other strong nucleophiles. In general, R is chosen to be a moiety that is neither nucleophilic nor electrophilic. In certain embodiments of the present invention R=straight-chain or branched alkyl, straight-chain or branched alkenyl, aryl, alkyl substituted aryl, aryl substituted alkyl, oxyalkyl, oxyethyl, poly(oxyalkylene), and poly(oxyethyene). In certain preferred embodiments R=straight-chain or branched alkyl with chain lengths from 1 to 18 carbon atoms and straight-chain or branched alkenyl with chain lengths from 1 to 18 carbon atoms. In certain other preferred embodiments R=straight-chain or branched alkyl with chain lengths from 1 to 12 carbon atoms and straight-chain or branched alkenyl with chain lengths from 1 to 12 carbon atoms. Particularly useful monomers for the synthesis of polymers of the present invention are 1,6:2,3-dianhydrohexopyranose monomers of structural formula (I) wherein R=allyl or benzyl.

Certain monomers particularly useful for the synthesis of polymers of the present invention are the 1,6:2,3-dianhydrohexopyranose monomers of structural formula (I) presented in Table 1, wherein the functional group is presented in the column headed "R" and a short-hand designation corresponding to each monomer is presented in the column headed "Notation". The "Notations" of shown in Table 1 are used to indicate the functional groups of the compounds described in the Examples presented in this specification.

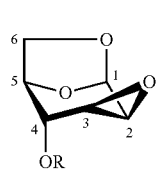
(I)

TABLE 1

| R = | Notation |
|---|---|
| —CH$_3$ | O |
| ~~~O~CH$_3$ | M |
| ~~~O~~~O~CH$_3$ | D |
| ~~~O~~~O~~~O~CH$_3$ | T |
| —(CH$_2$)$_3$CH$_3$ | Bu |
| —(CH$_2$)$_4$CH$_3$ | P |
| —(CH$_2$)$_5$CH$_3$ | H |
| —(CH$_2$)$_7$CH$_3$ | Oc |
| —(CH$_3$)$_9$CH$_3$ | Dc |
| ~~~= | A |
| >=< | Ip |
| ~< | Ib |
| ~~| | Ia |
| ~~~>< | Np |
| —CH$_2$Ph | B |
| ~~~O~~= | Ae |

TABLE 1-continued

| R = | Notation |
|---|---|
| (tetrahydrofuran with ethyl) | Tf |
| —O—(CH$_2$)$_4$—O— | pTHF |

Polymers resulting from the anionic, ring-opening, living polymerization of monomers of formula (I) are represented by the general structural formula (II), wherein n represents the average number of monomer units in a polymer chain.

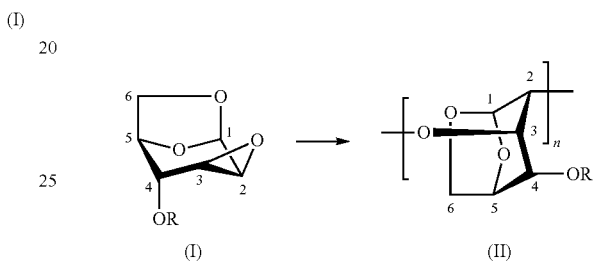

(I)          (II)

The overall synthesis of a poly(2-3)-1,6-anhydro-4-O-ß-D-glucopyranose of formula (II) by the anionic, ring-opening polymerization of a 1,6:2,3-dianhydrohexopyranose of formula (I) is illustrated in Reaction Scheme A. In this reaction sequence, the anionic initiator A⁻ attacks the 1,6:2,3-dianhydrohexopyranose (I) at C-2 opening the 2-3 epoxy ring to afford the alkoxyl anion of formula (III) which subsequently the attacks a second molecule of (I) in a like manner to open the 2-3 epoxy ring forming an ether linkage and a new alkoxyl anion of formula (IV) to begin the living polymerizing chain. This sequence of steps continues until all monomer is consumed and a high polymer is produced. It is important to note that such a living polymerization can be stopped at anytime by starving the reaction mixture of monomer at which time the growing polymer chain has a 'living end' and that the polymerization resumes when new monomer is introduced. The new monomer may be the same as the initial monomer or may be any other suitable monomer. Furthermore, two or more suitable monomers may be present in the initial reaction mixture, wherein the structure of the resulting copolymer is controlled by the concentrations and relative reactivity of the monomers. Since such a living polymerization adds monomers to a growing chain in serial fashion, molecular weight and copolymer composition are precisely controlled. Also, initiation of such living polymerizations can occur heterogeneously, i.e. from suitably reactive surfaces or in networks with suitable reactive sites such as anions.

Reaction Scheme A

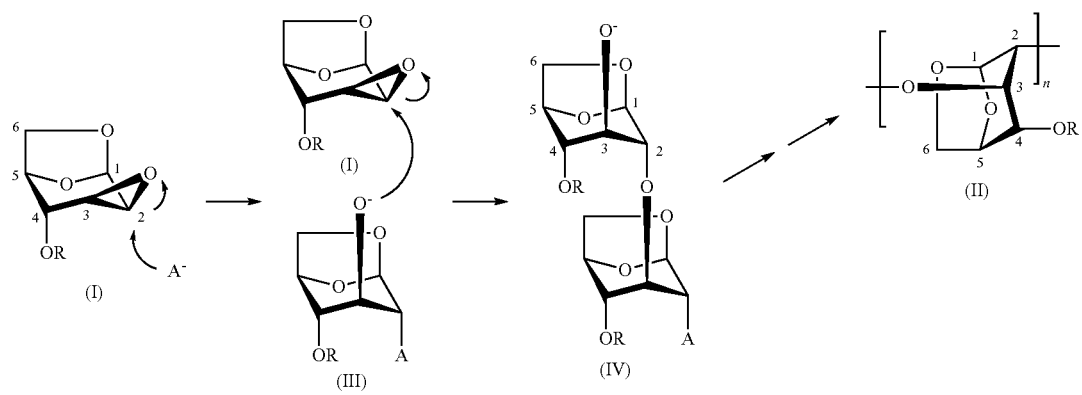

Certain polymers useful for embodiments of the present invention may include, but are not limited to, carbohydrate polyether-based polymers described in U.S. Pat. Nos. 7,994,092 and 8,642,502 and US Pub. Patent Application No. 20120046435, which are all herein incorporated in their entirety.

In certain embodiments of the present invention the carbohydrate polyethers are water-soluble, while in certain other embodiments the carbohydrate polyethers are water-insoluble and in still other embodiments the carbohydrate polyethers produce aqueous emulsions, dispersions or suspensions. In essence the relative hydrophilicity/hydrophobicity of the carbohydrate polyethers of the present invention is controlled via selection of the functionality at one or more of the C-1, C-4 and C-6 positions on the glucopyranose rings and the number of rings so functionalized, i.e. the concentration of the functionality. By such selection techniques compositions can be prepared to provide aqueous solutions, aqueous emulsions, aqueous suspensions or non-aqueous solutions.

Certain embodiments of the present invention utilize copolymers comprising one or more the general structures (II) (V), (VI), (VII) and (VIII). Wherein in certain embodiments R, $R_1$, $R_2$, $R_3$, $R_4$, $R_5$, $R_6$, $R_7$ and $R_8$ are moieties chosen to render the C2-C3 linked polyether of a 1,6:2,3-dianhydrohexopyranose derivative insoluble in aqueous media. Such aqueous insoluble polymers can be designed to be soluble in aqueous miscible solvents such as dimethyl sulfoxide, alcohols and the like.

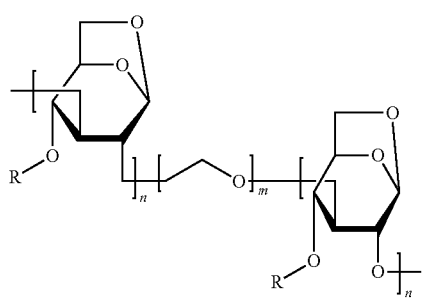
(V)

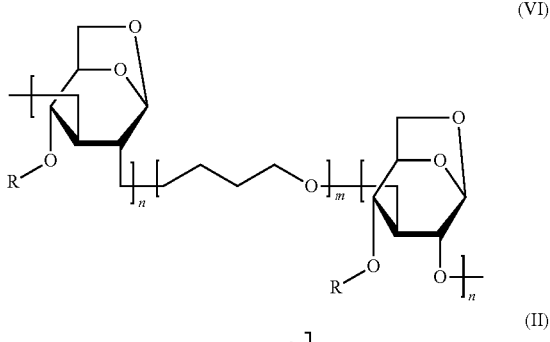
(VI)

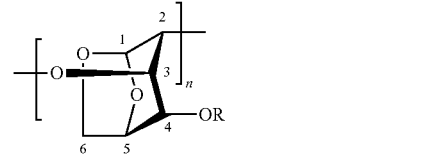
(II)

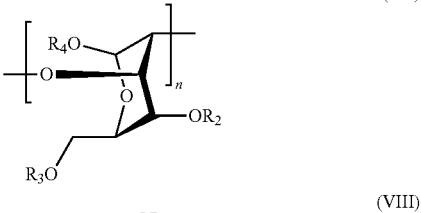
(VII)

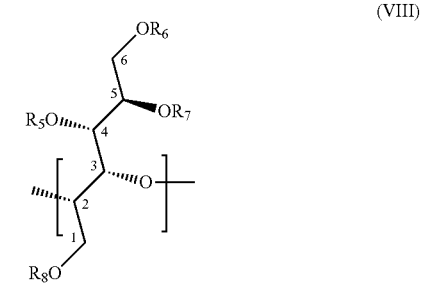
(VIII)

Certain polymer compositions useful in certain embodiments utilize polyurethane linkages, wherein such compositions are prepared by the reaction of copolymers of structure (V) or (VI) with a suitable diisocyanates including, but not limited to, toluene diisocyanate (TDI) and methylene diphenyl diisocyanate (TDI). Still other embodiments of the present invention utilize polymer compositions prepared by the reaction of copolymers of structure (V) or (VI) with suitable diacid halides to produce polyester linkages. Suitable diacid halides include, but are not limited to, glutaryl dichloride, adipoyl chloride, fumaryl chloride, terephthaloyl chloride, isophthaloyl chloride and sebacoyl chloride. Although the suitable chlorides have been listed above, the other halides, especially the bromides but also the fluorides and iodides, may be suitably substituted for the chlorides to obtain suitable polyester compositions. The preparation of such polyurethane and polyester compositions is illustrated in reaction scheme B, wherein toluene diisocyanate reacts with copolymers of structure (V) or (VI) to produce a polyurethane compositions and glutaryl dichloride reacts with copolymers of structure (V) or (VI) to produce a polyester composition. In such compositions the rate of biodegradability is controlled by the value of m, i.e. the chain length of the polyether segments —$(CH_2)_x$—O—.

particularly useful initiator, since the resulting allyl ether end-group is easily converted a variety of other functionalities.

Examples of functional termination agents for the anionic ring-opening polymerizations herein described include, but are not limited to, alkyl halides, acyl halides, acid anhydrides, aldehydes, ethylene sulfide, ethylene oxide, 1,3-dibromoethane and 3-bromomethylpropyonate.

In certain preferred embodiments, C2-C3 linked carbohydrate polyethers compositions and derivatives thereof the present invention are covalently coupled or crosslinked to from a self-supporting macro-reticular network. The required covalent coupling or crosslinking can be effected by any known method. For example, free-radical crosslinking can be effected by suitable chemical processes, suitable irradiation processes or combinations thereof. Suitable chemical free-radical initiators include azobisisobutyroni- Reaction Scheme B

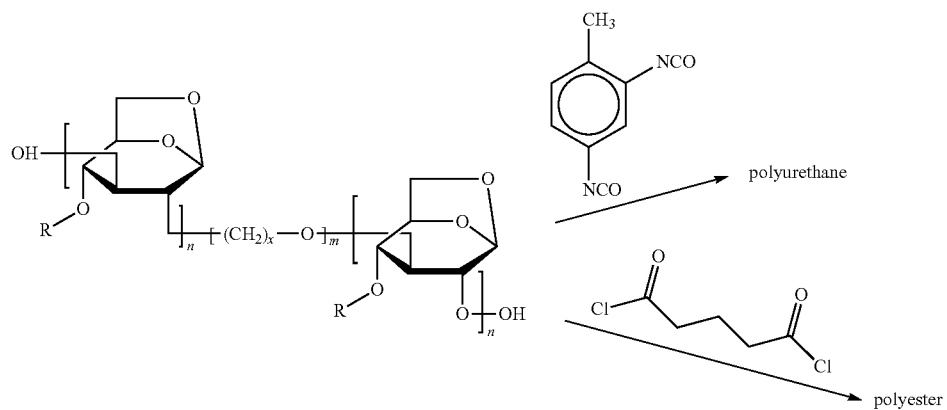

x = 2 or 4

In certain embodiments of the invention the biocompatible carbohydrate polyether-based polymers are designed to be biodegradable or bioresorbable, wherein the rates of such bioresorption or biodegradation of such polymers may be controlled by the choice of constituent moieties, molecular weight, polydispersity linearity, branching and the like.

In general, functional groups may be introduced at the chain-ends of the carbohydrate polyethers of the present invention by the use of specific initiation or termination agents, while functionality along the polymer chain may be introduced or modified by post-polymerization reactions. This ability to introduce selective functionality into the polymers allows for the preparation of carbohydrate polyethers useful in the preparation of protein, peptide and drug conjugates. Polymers with non-reactive moieties such as alkyl at one terminus of the polymer chain are particularly useful for the homogeneous preparation of conjugates in the absence of cross-linking reactions. In certain embodiments, polymers of the present invention can be prepared with distinct reactive functional groups at the chain ends, wherein such heterobifunctional polymers are useful for applications such as targeted drug delivery and biosensors.

Examples of functional initiators for the anionic ring-opening polymerizations herein described included, but are not limited to, potassium 3,3-diethoxypropanolate, potassium 2-buthoxy ethanolate, dipotassium 3-thiolate-1-propionate and potassium allyl alkoxide. Allyl alkoxide is a trile (AIBN), benzoyl peroxide and the like. Suitable high-energy irradiation sources include electron beam, ultraviolet (UV) and gamma irradiation. Additionally, crosslinking promoters such as bifunctional, trifunctional or tetrafunctional acrylates or methacrylate monomers and oligomers may be added to increase crosslinking efficiency and crosslink density. In other embodiments, self-supporting macro reticular networks are be produced by the covalent coupling or crosslinking blends of carbohydrate polyethers of the present invention with suitable active oligomers or polymers.

Certain preferred carbohydrate polyethers of the present invention are random copolymers, terpolymers and the like or block polymers. Certain of these polymers are thermosensitive polymers with gel transition temperatures in the range of 17° C. to 57° C.

The process used to combine certain carbohydrate polyethers of the present invention with one or more biologically active agents or other materials involves dissolution of the polymer followed by addition of the biologically active agent (in solution, suspension or powder), followed by thorough mixing to assure a homogeneous mixing of the biologically active agent throughout the polymer. Alternatively, the process can involve the dissolving of the polymer in a biologically active agent-containing solution. The biologically active agent will generally have a concentration in the range of 0 to 200 mg/ml. However, higher concentrations of the biologically active agent may be required in certain embodiments and are therefore not excluded.

The preferred range of molecular weights for certain carbohydrate polyethers useful in the present invention can be readily determined by a person skilled in the art based upon such factors as the desired polymer degradation rate, viscosity, polymer concentration in the solution. In certain medically useful compositions the polyether of a 1,6:2,3-dianhydrohexopyranose derivative has a molecular weight in the range of about 1 to 350 kDa. Typically, the preferred range of molecular weight will be 1 to 150 KDa, although there is no actual limitation.

Certain of the polyether of a 1,6:2,3-dianhydrohexopyranose useful in embodiments of the present invention have a polydispersity index (PDI) of less than or equal to 1.5. Wherein certain preferred polymer compositions have a PDI within the range of about 1.05 to 1.15.

Certain compositions of the present invention are particularly useful in medical procedures as embolic agents. Embolization is a term used to designate a nonsurgical, minimally invasive procedure, most commonly performed by interventional radiologists, that involves the selective occlusion of an area of a mammalian blood vessel by introducing or inducing emboli, which occlude the selected area of the vessel. Embolization procedures have been used to treat a wide variety of conditions affecting different organs of the human body, including, but not limited to, recurrent hemoptysis, arteriovenous malformations (AVMs), cerebral aneurysm, gastrointestinal bleeding, epistaxis and the like. Such embolic procedures are also used to slow or stop blood supply thus reducing the size of the tumors including kidney lesions, liver lesions and hepatocellular carcinoma (HCC). Also treated either by particle infarction or transcatheter arterial chemoembolization (TACE) are uterine fibroids and malignant hypertension due to end stage renal failure. Tumor embolizations are used to preoperatively treat meningiomas, hemangioblastomas, renal cell metastases, and paragangliomas. In certain of such embodiments the biocompatible carbohydrate polyether-based polymers are biodegradable or bioresorbable.

Certain embodiments of the present invention are useful in medical applications such as embolization of a blood vessel or treatment of urinary incontinence. In such embodiments the compositions comprise a solution of an aqueous insoluble C2-C3 linked polyether of a 1,6:2,3-dianhydrohexopyranose derivative dissolved in a biocompatible solvent, wherein the biocompatible solvent may be aqueous soluble, aqueous insoluble, or aqueous miscible. In certain preferred embodiments the biocompatible solvent is an aqueous miscible solvent. Embolization of blood vessels is preferably accomplished via catheter techniques, which permit the selective placement of the catheter and introduction of the embolic composition to the vascular site to be embolized. In certain embodiments the biocompatible solvent may be dimethylsulfoxide (DMSO) or ethanol or in certain embodiments aqueous solutions of ethanol or DMSO.

In a particularly preferred embodiment, the embolic composition further comprises a contrast agent and, in particular a water insoluble contrast agent. The contrast agent is employed in order that the physician can visualize delivery of the embolic composition to the vascular site via conventional techniques such as fluoroscopy.

In certain a typical embodiment of an embolic procedure of the present invention, the embolic solvent is selected to be miscible or soluble in blood or other body fluid and to solubilize the water insoluble biocompatible polymer during delivery. The biocompatible polymer is selected to be soluble in the embolic solvent but insoluble in blood or other body fluid. A contrast agent is suspended or dissolved in the composition and, as above, is selected to permit the physician to fluoroscopically visualize catheter delivery of this composition. Such a contrast agent may be aqueous soluble or aqueous insoluble. Upon contact with the blood or other body fluid, the embolic solvent dissipates from the embolic composition whereupon the biocompatible polymer precipitates in the presence of the water insoluble contrast agent and embolizes or occludes the blood vessel. The quantity of embolic composition used in a procedure is selected to be sufficient to embolize or occlude the selected area of the vessel. Preferred contrast agents for such procedures include, but are not limited to, tantalum, tantalum oxide, tungsten and barium sulfate.

Certain embodiments of the invention are useful in methods for treating urinary incontinence in a mammal, which method comprises delivering a composition comprising an aqueous insoluble C2-C3 linked polyether of a 1,6:2,3-dianhydrohexopyranose derivative, a biocompatible solvent, and an optional contrast agent to the periurethral tissue of the mammal Certain embodiments are useful as biological scaffolds in wound healing applications, while other embodiments are useful for encapsulation of mammalian cells.

Certain compositions of the present invention are useful as vehicles for drug delivery applications as controlled release agents. Certain of these preferred drug delivery compositions comprise biocompatible carbohydrate polyether-based polymers, which in certain embodiments are biodegradable or bioresorbable. In certain embodiments such biocompatible carbohydrate polyether-based polymers are water-insoluble. Such drug delivery compositions further comprise one or more bioactive agents. In certain preferred drug-delivery compositions the carbohydrate polyether-based polymers are used in the form of particles, solid microspheres, porous microspheres, microcapsules, implantable devices such as stents, films, foams, coatings and the like, all which can be formed by known means including, but not limited to, phase separation, precipitation, extrusion, solution casting, membrane emulsification, evaporation methods, spray drying, and emulsification. In certain embodiments such physical forms can be tailored to provide predictable time-related gradual release profile of the bioactive agent. In certain embodiments useful microparticles can have average diameters in the range from 2μ to 400μ, preferably 10μ to 50μ.

Certain compositions of the present invention are useful as medical implants including, but not limited to, subcutaneous implants, sub-renal capsules, intrahepatic implants, intravenous and intra-arterial implants, intramuscular implants, implantation into the wall of the stomach, small intestines or large intestines, intracranial implants, bone marrow or spleen implants, visceral tissue or organ implants and the like. Solid implants can be formed in situ by injecting a solution of a polymer composition of the present invention and one or more bioactive agents in an organic solvent to a selected site in a mammalian body, wherein the polymer precipitates. In certain embodiments such a delivery method is particularly useful for controlled drug release applications. In certain other embodiments the polymers are liquid at or about room temperature and are capable of remaining gels or solids at or below body temp. Slow drug release is enabled by such embodiments.

In certain drug delivery compositions the bioactive agent is a small molecule drug including, but not limited to, acne reducing drugs, antibiotics, antivirals, antifungals, antineoplastics, antiangiogenics, antiarrhythmics, antiparkinson drugs, anticoagulants, anticonvulsants, anticancer drugs, antiallergic drugs, antidepressants, antidiabetic drugs, antihistamines, antihypertensives, antimigraine drugs, antipsychotics, anxiolytics, sedatives, hypnotics, bile acid sequestrants, bisphosphonates, bone resorption inhibitors, bronchodilators, lipid-lowering drugs, cardiovascular drugs, central nervous system drugs, chelating agents, cholesterol absorption inhibitors, contraceptives, decongestants, dermatological agents, diagnostic agents, radiopharmaceuticals, diuretics, expectorants, drugs used in treating alcohol, tobacco and illegal drug dependence, fibric acid drugs, gastrointestinal drugs, general anesthetics, growth hormones, heparins, heparin antagonists, herbal products, immunologic agents, immunosuppressants, insulin, inotropic agents, interferons, mast cell stabilizers, mouth, nose and throat drugs, muscle relaxants, nutritional products, ophthalmic drugs, antibiotic drugs, probiotics, psychotherapeutic drugs, radiological agents, respiratory drugs, sex hormones, spermicidal agents, statins, thrombolytics, thyroid drugs, vaginal preparations, vitamins and the like.

Certain compositions of the present invention are useful as injectables for subdermal maxiofacial applications such as wrinkle fill, lip augmentation, agents for reduction of folds, agents for removal of scars and the like.

Certain compositions of the present invention are useful for augmentation of mammalian body tissue in surgical procedures including, but not limited to, organ restoration, breast volume enhancement, eye surgery, knee restoration, ulcer treatment, AVM and aneurism treatments and the like. Certain compositions of the present invention are useful surgical procedures involving the eye including, but not limited to, corneal transplantation, cataract surgery, glaucoma surgery and surgery to repair retinal detachment. While certain other compositions of the present invention are useful as non-inflammatory vitreous substitutes to prevent scrapping of the endothelial cells as well as injectable agents for the treatment of arthritis particularly osteoarthritis of the knee.

Certain compositions of the present invention are useful in tissue engineering applications for the synthesis of biological scaffolds for wound healing applications and to facilitate cell migration into the wound treatment. Yet other compositions of the present invention are useful in combination with sodium bicarbonate or other agents to treat acid reflux and diarrhea.

Certain embodiments of the present invention provide reagents, polymers, encapsulated cells, capsules, and related method that result in reduced inflammation. Reduced inflammation can be assessed, for example, by comparing the inflammation associated with such embodiments with the inflammation induced by an implants comprising alginates, carrageenan, polyornithines, and the like. Certain preferred embodiments provide a level of inflammation from about 1% to 80% of the inflammation observed in a comparator composition, while certain other preferred embodiments provide a level of inflammation that is less than 10% of the inflammation observed in a comparator composition. Still other preferred embodiments provide a level of inflammation that is below the level of detection. In such an evaluation the inflammation the comparator composition can be a historic control such as described in Brody, T. (2012) *Clinical Trials (Study Design, Endpoints and Biomarkers, Drug Safety, as well as FDA and ICH Guidelines*, Elsevier/Academic Press, pp. 20, 109 and 131.

Certain particularly preferred embodiments of the present invention consist of biomedically useful compositions comprising an aqueous insoluble C2-C3 linked polyether of a 1,6:2,3-dianhydrohexopyranose derivative intimately associated with a bioactive agent; and wherein the aqueous insoluble C2-C3 linked polyether of a 1,6:2,3-dianhydrohexopyranose derivative has a physical form selected from the group consisting of microparticles, microspheres, tubes, rods, sheets, membranes and fibers. In certain embodiments the physical form of the C2-C3 linked polyether of a 1,6:2,3-dianhydrohexopyranose derivative is porous. In certain embodiments the average pore diameters of the porous C2-C3 linked polyether of a 1,6:2,3-dianhydrohexopyranose derivative is in the range of 0.001 mm to 0.05 mm, preferably less than 0.02 mm, and more preferably less than 0.01 mm and most preferably less than 0.005 mm. In certain preferred embodiments the C3 linked polyether of a 1,6:2, 3-dianhydrohexopyranose derivative is in the form of microspheres having an average diameter between 20 μm to 2000 μm. In certain embodiments the bioactive agent is uniformly dispersed throughout the C2-C3 linked polyether of a 1,6: 2,3-dianhydrohexopyranose derivative. The composition of claim 1 wherein the C2-C3 linked polyether of a 1,6:2,3-dianhydrohexopyranose derivative is bioresorbable, while in other embodiments the bioactive agent is in the form of a coating on the surface of the C2-C3 linked polyether of a 1,6:2,3-dianhydrohexopyranose derivative. In certain embodiments the bioactive agent is aqueous soluble. In certain embodiments the bioactive agent is a protein and in certain embodiments the protein is chosen from the group consisting of X Y Z etc. In certain embodiments of the biomedically useful compositions of the present invention the C2-C3 linked polyether of a 1,6:2,3-dianhydrohexopyranose derivative is bioresorbable.

The following examples are presented as illustrations of embodiments of the present invention and should not be construed to limit the scope of the invention in any manner.

EXAMPLES

Example 1

Synthesis of 1,6-dianhydrohexopyranose monomers (designations: Ae, O, M and D)

1,6:2,3-dianhydro-4-O-(2-allyloxyethyl)-R-D-mannopyranose (monomer designation Ae)

A solution containing 199.7 g of 1,6:3,4-dianhydro-2-O-tosyl-ß-D-galactopyranose, 18.4 g of p-toluenesulfonic acid, 121 mL of toluene and 251 mL of 2-allyloxyethanol was stirred at 80° C. for 7 hrs. then cooled to room temperature. To this solution 20.3 g sodium in 250 mL of methanol was added over a period of 1 hr. and the resulting solution was stirred for 2 hrs., after which 600 mL of dichloromethane and 800 mL of a 5% solution of NaCl in $H_2O$ were added. The resulting organic layer was separated, and the aqueous layer was twice extracted with 100 mL portions of dichloromethane. Combined dichloromethane extracts were dried over anhydrous $MgSO_4$ and reduced in vacuo to afford a syrup. The syrup was distilled under high vacuum and further purified by a second distillation to afford a colorless liquid product. Yield=116 g (81%).

In a similar manner (as described U.S. Pat. Nos. 7,994, 092 and 8,642,502) the following monomers were synthesized:

1,6:2,3-dianhydro-4-O-methyl-R-D-mannopyranose (monomer O);
1,6:2,3-dianhydro-4-O-(2-methoxyethyl)-R-D-mannopyranose (monomer M); and
1,6:2,3-dianhydro-4-O-(2-(2-methoxyethoxy)ethyl)-R-D-mannopyranose (monomer D).

Example 2

Synthesis of a 1:1:1:1 Copolymer of Anhydrohexapyranose Monomers Ae, O, M and D of Example 1

A 10 mL reaction vessel was charged with 0.096 g of 1,6:2,3-dianhydro-4-O-methyl-ß-D-mannopyranose (monomer O), 0.139 g of 1,6:2,3-dianhydro-4-O-(2-allyloxyethyl)-ß-D-mannopyranose (monomer Ae), 0.123 g of 1,6:2,3-dianhydro-4-O-(2-methoxyethyl)-ß-D-mannopyranose (monomer M), 0.150 g of 1,6:2,3-dianhydro-4-O-(2-(2-methoxyethoxy)ethyl)-ß-D-mannopyranose (monomer D), 0.5 g of tetrahydrofuran (THF), and 48 mg of a 195 mM solution of potassium 2-butoxyethanolate in THF; and contents were mixed at room temperature to obtain a clear solution. Vessel was sealed and the reaction mixture was incubated at 55° C. for 12 hrs. The resulting polymer was recovered by the addition of 8 mL of deionized water and heating to 60° C. to effect precipitation of polymer which was then dried in vacuo for 24 hrs. Yield=0.507 g (99.7%), GPC analysis: Mw=53000, DP=260.

Example 3

In Vitro Evaluation of Copolymer of Example 2

A solution of 0.25 g of the 1:1:1:1 copolymer of dianhydrohexapyranoses monomers Ae, O, M and D polymer (of Example 2) in 1.0 g of dimethyl sulfoxide (DMSO) was extruded through a 0.027 inch ID×1.5 m length intracranial catheter (from Reverse Medical Corporation, Irvine, Calif.) into a 10 mL vial containing phosphate buffered saline (PBS) at 37° C. White spaghetti-like or bulbous embolic precipitates were immediately formed upon extrusion from the tip of the catheter. Upon storage in 37° C. phosphate buffered saline (PBS) for one week the morphology of the extruded polymer appeared unchanged.

Example 4

Synthesis of a 3:1 Copolymer of Dianhydrohexapyranose Monomers M and Ae of Example 1

A 70 mL reaction vessel was charged with 5.593 g 1,6:2,3-dianhydro-4-O-(2-methoxyethyl)-ß-D-mannopyranose (monomer M), 1.394 g 1,6:2,3-dianhydro-4-O-allyl-ß-D-mannopyranose (monomer A), 6.0 g of tetrahydrofuran (THF) and 0.586 g of 195 mM solution of potassium 2-buthoxyethanolate in THF. Vessel contents were mixed at room temperature to obtain a clear solution and then vessel was sealed and incubated at 55° C. for 12 hrs. Polymer was recovered by mixing the reaction mixture with 60 mL of deionized water and 0.2 mL of 1M acetic acid. The polymer was then precipitated at room temperature and precipitate was washed with 60 mL deionized water followed by vacuum drying for 24 hrs. Yield=6.04 g (100%).

Example 5

In Vitro Evaluation of the Composition of Example 4

A solution of 0.2645 g of the 3:1 copolymer of dianhydrohexapyranoses monomers M and Ae prepared in Example 1 was dissolved in 0.6358 g of DMSO and the resulting solution was extruded through a Reverse Medical 0.027 inch ID×1.5 m length intracranial catheter into 10 mL vial containing phosphate buffered saline (PBS) at 37° C. A white spaghetti-like precipitate was immediately formed upon extrusion from the tip of the catheter. The morphology of extruded polymer appeared to be unchanged after storage in 37° C. PBS for one week.

Example 6

Synthesis of 85 (M)-27 (pTHF)-85(M) Block Copolymer Diol 10 g Terathane® 2000 (polytetrahydrofuran, DPn=27, obtained from Invista, USA) was dried over 0.2 g of CaH2 at 60° C. for seven days. 1.17 g of the dried Terathane® 2000 and 21 mg of potassium metal were added to 4.998 g of THF and mixture was incubated at room temperature for 3 days to afford a solution. A 10 ml reaction vessel was charged with 0.871 g of this THF solution along with 0.508 g of 1,6:2,3-dianhydro-4-O-(2-nmethoxyethyl)-B-D-mannopyranose (monomer M from Example 1). The reactor contents were mixed at room temperature, after which the reactor was sealed and reaction mixture was incubated at 55° C. for 12 hrs. The resulting polymer was recovered by mixing the viscous crude reaction product with 8 mL of DI water, and 20 mg of 1M acetic acid. The polymer product was then precipitated at 50° C., precipitate was subsequently washed with 8 mL DI water and dried in vacuo for 24 hrs. Yield=5.32 g (106%). (LCST)=12.5° C. (15% in PBS)

Example 7

Synthesis of 155 (M)-27 (pTHF)-155 (M) Block Copolymer Diol

A 10 mL reaction vessel was charged with 0.482 g of a solution of potassium poly(tetrahydrofuran) in THF (prepared as in Example 6) and 0.514 g of 1,6:2,3-dianhydro-4-O-(2-methoxyethyl)-R-D-mannopyranose (monomer M prepared as in Example 1). The reactor contents were mixed at room temperature, after which reactor was sealed and reaction mixture was incubated at 55° C. for 12 hrs. Resulting polymer was recovered by mixing the viscous crude reaction product with 8 mL of DI water, and 20 mg of 1M acetic acid. Polymer product was precipitated at 50° C. and precipitate was washed with 8 mL DI water and dried in vacuo for 24 hrs. Yield=0.532 g (103.4%). Lower critical solution temperature (LCST)=17.5° C. (15% in PBS)

Example 8

Synthesis of 300(M)-27(pTHF)-300(M) Block Copolymer Diol

A 10 mL reaction vessel was charged with 0.248 g of a solution of potassium poly(tetrahydrofuran) in THF (prepared as in Example 6), 0.25 g of THF and 0.512 g of 1,6:2,3-dianhydro-4-O-(2-methoxyethyl)-R-D-mannopyranose (monomer M prepared as in Example 1). The reactor contents were mixed at room temperature, reactor was sealed and reaction mixture was incubated at 55° C. for 12 hrs. Resulting polymer was recovered by mixing the viscous crude reaction product with 8 mL of DI water, and 20 mg of 1M acetic acid. Polymer product was precipitated at 50° C. and precipitate was washed with 8 mL DI water and dried in vacuo for 24 hrs. Yield=0.520 g (101.6%). Lower critical solution temperature (LCST)=23° C. (15% in PBS).

Example 9

Infusion of Polymer Beads with a Biological Agent

A solution was prepared from 12 mg of egg white lysozyme in 100 uL of deionized water. This solution was then added a solution of 400 mg of a poly(2-3)-1,6-anhydro-4-O-octyl-ß-D-glucopyranose (Oc) homo polymer in 4 g of $CH_2Cl_2$ to emulsified for 1 min using an IKA T-25 high-speed homogenizer at 18,000 rpm to afford a primary emulsion. This primary emulsion was poured into 60 mL of a 1% aqueous solution of polyvinyl alcohol and stirred at 2000-2500 rpm for 3 min resulting in a secondary emulsion. The secondary emulsion was washed with 400 mL of deionized water for 4 hrs. to afford a suspension of egg white lysozyme infused beads, which was centrifuged at 2500 rpm, washed with water and freeze dried. Round egg white lysozyme infused beads were obtained with a mean particle size 25-50 μm. The resulting egg white lysozyme infused beads were loaded into 10 mL vials containing 2 mL of PBS each, crimped and incubated at 37° C. The release the egg white lysozyme from the polymer beads was measured as a function of time.

Example 10

Infusion of Polymer Films with a Biological Agent

A solution was prepared from 12 mg of egg white lysozyme in 100 uL of deionized water. This solution was then added a solution of 400 mg of a t-AM polymer (of composition: 23% wt % of poy(2-3)-1,6-anhydro-4-O-allyl-ß-D-glucopyranose and 77% wt % of poy(2-3)-1,6-anhydro-4-O-(2-methoxyethyl)-R-D-glucopyranose) in 4 g of $CH_2Cl_2$ and emulsified for 1 min using an IKA T-25 high-speed homogenizer at 18,000 rpm to afford a primary emulsion. This primary emulsion volume was poured into the two 28×28 mm Teflon® trays and dried overnight at RT to afford in egg white lysozyme infused polymer films. The films were cut into strips weighing 80-100 mg each. The resulting egg white lysozyme infused film strips were loaded into 10 mL vials containing 2 mL of PBS each and incubated at 37° C. The release the egg white lysozyme from the polymer film-strips was measured as a function of time.

Example 11

Protein Measurement

Total protein was measured by UV adsorption at 280 nm, calibrated with bicinchoninic acid (BSA) or lysozyme. This method is also referred to as BCA assay or the Smith assay. (Smith, P. K., et al. *Anal. Biochem.* 1985, 150 (1): 76-85.

Active protein was measured by optical density kinetics at 450 nm using *Micrococcus lysodeikticus* suspensions and a known amount of lysozyme (available from Sigma, St. Louis)

Example 12

Preparation of Aminated Polymers for Use in Hernia Mesh Fixation or as a Surgical Adhesive or Glue.)

A solution of 0.25 g of a 55O-15Ae-30D terpolymer in 0.25 g of THF was diluted with 2.0 g of diglyme and 0.185 g of a 0.627 mM/kg solution of $BF_3.(CH_3)_2S$ (boron trifluoride methyl sulfide complex available from Sigma-Aldrich USA) in THF was added and mixture was allowed to stand overnight at RT, after which 30 mg of a 12% solution of HOA (Hydroxylamine-O-sulfonic acid) in diglyme was added and resulting mixture was vortexed. Mixture was then incubated for 12 hrs. after which 0.55 g of 2M NaOH and 67 mg of $H_2O_2$ was added resulting in a clear colorless solution. The polymer product was recovered by 10 volume washing with DI water using Pierce 20 KDA MWCO concentrators and lyophilization resulting in 0.161 g of white polymer with ~5 mole % of monomer units containing primary amine (as determined by titration).

A similar experiment was performed with an Ae homopolymer resulting in a product with ~18 mole % of the monomer units containing primary amine (as determined by titration).

Example 13

Use of Animated Polymers for Hernia Mesh Fixation or as Surgical Adhesive

A mixture of N-hydroxysuccinimide (NHS) activated bifunctional polyethylene glycol (PEG, MW=3400) and the aminated polymers from Example 13 in PBS afforded in a solution having a ~1/1 —$NH_2$/NHS molar ratio and a 10-20% total polymer content. The solution exhibited a 1-5 min gelation reaction time. Pull shear tests were performed by applying 1 mL of adhesive formulation onto a 3×2.5 cm nylon hernia mesh on a pig skin soaked in PBS and blotted at RT followed by incubation at 37° C. for 5 min. A pull test at 0.42 cm/min (Instron® tensile apparatus utilizing Blue Hill® software) showed a minimum pull strength of 0.8 N and a maximum pull strength of 10.7 N.

Example 14

Preparation of Monomer 1,6:2,3-dianhydro-4-O-(n-decyl)-ß-D-mannopyranose (Dc)

A solution of 201.4 g of 1,6:3,4-dianhydro-2-O-tosyl-R-D-galactopyranose, 15 g of p-toluenesulfonic acid, 149 mL of toluene and 428 g of n-decanol was stirred at 80° C. for 7 hrs. After cooling to RT the solution of 20.4 g sodium in 245 mL of methanol was added in 1 hr. and stirred for two hrs. at RT. DCM (600 mL) and water (800 mL with 5 of NaCl) were added, the organic layer was separated, and water layer was extracted with 2×100 mL of DCM. Combined DCM extract was dried over MgSO4 and reduced in vacuo to syrup. The syrup was distilled under high vacuum and further purified by second distillation. Yield=151.1 g (79%); colorless liquid. Spec. Rotation ($CH_2Cl_2$)=24.8°

Example 15

Preparation of t-DcB Copolymer (16 wt % of Monomer Dc)

A reaction mixture of 1,6:2,3-dianhydro-4-O-n-decyl-R-D-mannopyranose (Dc, 0.095 g), 1,6:2,3-dianhydro-4-O- benzyl-R-D-mannopyranose (B, 0.503 g, 0.5 g of tetrahydrofuran (THF), 100 mg of 57 mM solution of potassium 2-buthoxyethanolate in THF were loaded into 10 mL reaction vessel, mixed at room temperature to obtain a clear solution, sealed and incubated at 60° C. for 14 hrs. Polymer was recovered by mixing the reaction mixture with 20 mL of ethanol, precipitating polymer and vacuum drying the polymer for 24 hrs. Yield=0.59 g (98%), GPC analysis: Mn=32544, Mw=35399

Example 16 t-DcB Copolymer Polymer Films Loaded with a Biological Agent/Drug 12 mg of egg white lysozyme was dissolved in 100 uL of DI water and emulsified for 1 min into the solution of 400 mg of the t-DcB polymer in 4 g of DCM using IKA T25 mixer at 18000 rpm. The emulsion volume was poured into the two 28×28 mm PTFE trays and dried overnight at RT. The two plastic films were detached from the tray, edges were cut by scissors and 6 strips were cut from the flat portions of the films 80-100 mg each. The film strips were loaded into two 10 mL vials with 2 mL of PBS each, crimped and incubated at 37° C. for time points at which PBS solution was removed and a new one added. Total released protein and active released protein were measured in each liquid sample to generate time-release data presented in Table. 2

TABLE 2

(Release of the lysozyme from t-DcB copolymer)

| Day, n | Total Protein, % | Day, n | Active Protein, % |
|---|---|---|---|
| 1 | 1.7 | 0 | 63 |
| 28 | 12.1 | 1 | 52 |
| 84 | 32.8 | 20 | 61 |
| 134 | 46.3 | 100 | 60 |

Example 17

Synthesis of t-H Polymer (100 wt % of Monomer H)

1,6:2,3-dianhydro-4-O-n-hexyl-ß-D-mannopyranose (H, 1.03 g), 1.0 g of tetrahydrofuran (THF), 86 mg of 174 mM solution of potassium 2-buthoxyethanolate in THF were loaded into 10 mL reaction vessel, mixed at room temperature to obtain a clear solution, sealed and incubated at 60° C. for 14 hrs. Polymer was recovered by mixing the reaction mixture with 20 mL of ethanol, precipitating polymer and vacuum drying the polymer for 24 hrs. Yield=1.0 g (99%), Spec Rotation ($CH_2Cl_2$)=−71.6°. GPC analysis: Mn=65000.

Example 18

T-H Polymer Films Loaded with a Biological Agent/Drug 12 mg of egg white lysozyme was dissolved in 100 uL of DI water and emulsified for 1 min into the solution of 400 mg of the t-H polymer in 4 g of DCM using IKA T25 mixer at 18000 rpm. The emulsion volume was poured into the two 28×28 mm PTFE trays and dried overnight at RT. The two plastic films were detached from the tray, edges were cut by scissors and 6 strips were cut from the flat portions of the films 80-100 mg each. The film strips were loaded into two 10 mL vials with 2 mL of PBS each, crimped and incubated at 37° C. for time points at which PBS solution was removed and a new one added. Total released protein and active released protein were measured in each liquid sample to generate time-release data shown in Table 3.

TABLE 3

(Release of the lysozyme from t-H polymer)

| Day, n | Total Protein, % | Active Protein, % |
|---|---|---|
| 3 | 9 | 102 |
| 27 | 22.2 | 91 |
| 100 | 33 | 82 |

Embodiments of the invention being thus described, it will be obvious that the same may be varied and that such variations are not to be regarded as a departure from the spirit and scope of the invention and all such modifications are intended to be included within the scope of the following claims.

I claim:
1. A biomedically useful composition comprising:
a C2-C3 linked polyether of a 1,6:3,3-dianhydrohexapyranose comprising one or more monomeric units selected from the group consisting of a monomeric unit of the structural formula

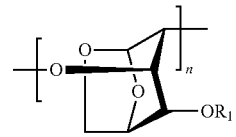

a monomeric unit of the structural formula

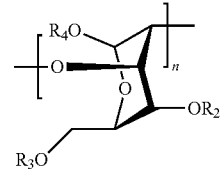

and a monomeric unit of the structural formula

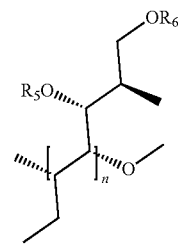

wherein $R_1$, $R_2$, $R_3$, $R_4$, $R_5$, $R_6$, $R_7$ and $R_8$ are moieties that to render said C2-C3 linked polyether insoluble in aqueous media chosen from the group consisting of:

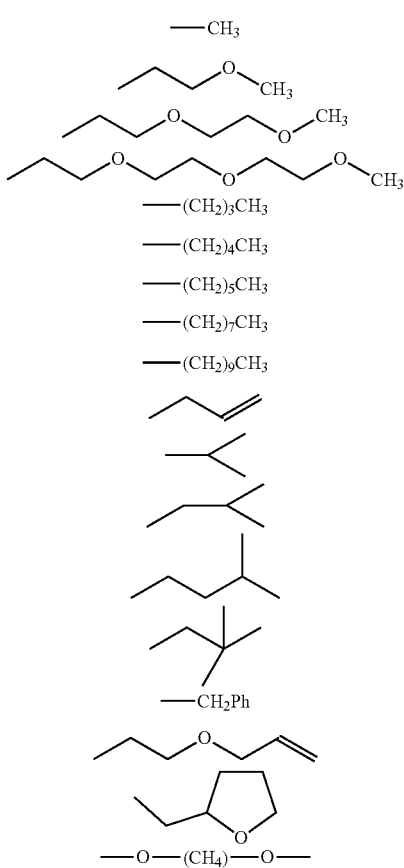

and, further comprising an effective amount of at least one bioactive agent.

2. The composition of claim 1 wherein the bioactive agent is uniformly dispersed throughout the C2-C3 linked polyether of a 1,6:3,3-dianhydrohexapyranose.

3. The composition of claim 1 wherein the bioactive agent is intimately associated with the C2-C3 linked polyether of a 1,6:3,3-dianhydrohexapyranose.

4. The composition of claim 1 wherein the C2-C3 linked polyether of a 1,6:3,3-dianhydrohexapyranose is bioresorbable.

5. The composition of claim 1 wherein the bioactive agent is comprises a coating on the surface of the C2-C3 linked polyether of a 1,6:3,3-dianhydrohexapyranose.

6. The composition of claim 1 wherein the bioactive agent is soluble in aqueous media.

7. The composition of claim 1 wherein the bioactive agent is a protein.

8. The composition of claim 7 wherein the protein is chosen from the group consisting of enzymes, monoclonal antibodies, fusion proteins, VeGF and VEGF inhibitors.

9. The composition of claim 1 wherein the bioactive agent is a small molecule drug.

10. The composition of claim 1 wherein the composition has a physical form of microparticles or microspheres having an average diameter between 100 and 1000 microns.

11. The composition of claim 10 wherein the bioactive agent is a protein.

12. The composition of claim 10 wherein the bioactive agent is soluble in aqueous media.

13. The composition of claim 1 wherein the bioactive agent has a physical form selected from the group consisting of microparticles, microspheres, tubes, rods, sheets, membranes and fibers.

14. The composition of claim 1 wherein the bioactive agent has a physical form of microparticles or microspheres.

15. The composition of claim 1 wherein the microparticles or microspheres have an average diameter between 5 and 2000 microns.

16. The composition of claim 1 wherein the physical form of the bioactive agent is porous.

17. The composition of claim 1 wherein bioactive agent has a total pore volume in the range of 0.05 cc/g to 5.0 cc/g.

* * * * *